(12) United States Patent
Peregrino Ferreira et al.

(10) Patent No.: US 7,026,133 B2
(45) Date of Patent: *Apr. 11, 2006

(54) METHOD AND COMPOSITION FOR THE DIAGNOSIS OF EQUINE INFECTIOUS ANEMIA VIRUS DISEASE BY USING THE RECOMBINANT CAPSID PROTEIN VIRUS (P26)

(75) Inventors: Paulo César Peregrino Ferreira, Belo Horizonte (BR); Erna Geessien Kroon, Belo Horizonte (BR); Jenner Karlisson Pimenta Dos Reis, Belo Horizonte (BR); Isabella Bias Fortes Ferraz, Belo Horizonte (BR); Rômulo Cerqueira Leite, Belo Horizonte (BR)

(73) Assignee: Universidade Federal de Minas Gerais, Belo Horizonte (BR)

( * ) Notice: Subject to any disclaimer, the term of this patent is extended or adjusted under 35 U.S.C. 154(b) by 218 days.

This patent is subject to a terminal disclaimer.

(21) Appl. No.: 10/461,360

(22) Filed: Jun. 16, 2003

(65) Prior Publication Data

US 2003/0207261 A1 Nov. 6, 2003

Related U.S. Application Data

(60) Division of application No. 09/759,281, filed on Jan. 16, 2001, now Pat. No. 6,596,846, which is a continuation-in-part of application No. 09/331,262, filed as application No. PCT/BR97/00081 on Dec. 19, 1997, now abandoned.

(51) Int. Cl.
*G01N 33/543* (2006.01)

(52) U.S. Cl. .......................... 435/7.92; 435/5; 435/7.1; 435/7.9; 530/350

(58) Field of Classification Search .................. 435/5, 435/7.1, 7.9, 7.92; 530/350
See application file for complete search history.

(56) References Cited

U.S. PATENT DOCUMENTS

| 3,932,601 | A | | 1/1976 | Coggins |
| 4,806,467 | A | | 2/1989 | Porter et al. |
| 5,427,907 | A | | 6/1995 | Peterson et al. |
| 6,596,846 | B1 | * | 7/2003 | Peregrino Ferreira et al. ... 530/350 |

OTHER PUBLICATIONS

Shen et al., *American Journal of Veterinary Research*, vol. 45, No. 8, 1984, pp. 1542–1543.
Reis et al., 1996 *Genbank ACC.*, No. U53452.
Payne et al., *Virology 172*, 1989, pp. 609–615.
Birkett et al. (Biochemica et Biophysica Acta vol. 1339 No. 1, pp. 62–72, Apr. 25, 1997).
Kong et al. (Microbiology and Immunology, vol. 41 No. 12, pp. 975–980, 1997).

* cited by examiner

*Primary Examiner*—Mark Navarro
*Assistant Examiner*—Robert A. Zeman
(74) *Attorney, Agent, or Firm*—Young & Thompson

(57) ABSTRACT

The present invention relates to a method and kit for detecting antibodies in clinical samples of animals infected with equine infectious anemia virus using the immunodiagnosis with the recombinant viral antigen p26. The antigen was bound to solid supports (microtiter plates, tubes, beads or nitrocellulose papers or nylon) and reacted with the test serum. After incubation with conjugated anti-equine immunoglobulin-enzyme the reaction was revealed with a solution composed of the substrate of the enzyme used in the conjugate (cromogene). After development of the reaction (color formation) it was stopped with acid solution and measured. The immunoassay may be a direct second antibody immunoassay, a one or two step sandwich immunoassay.

7 Claims, 3 Drawing Sheets

Figure 1:
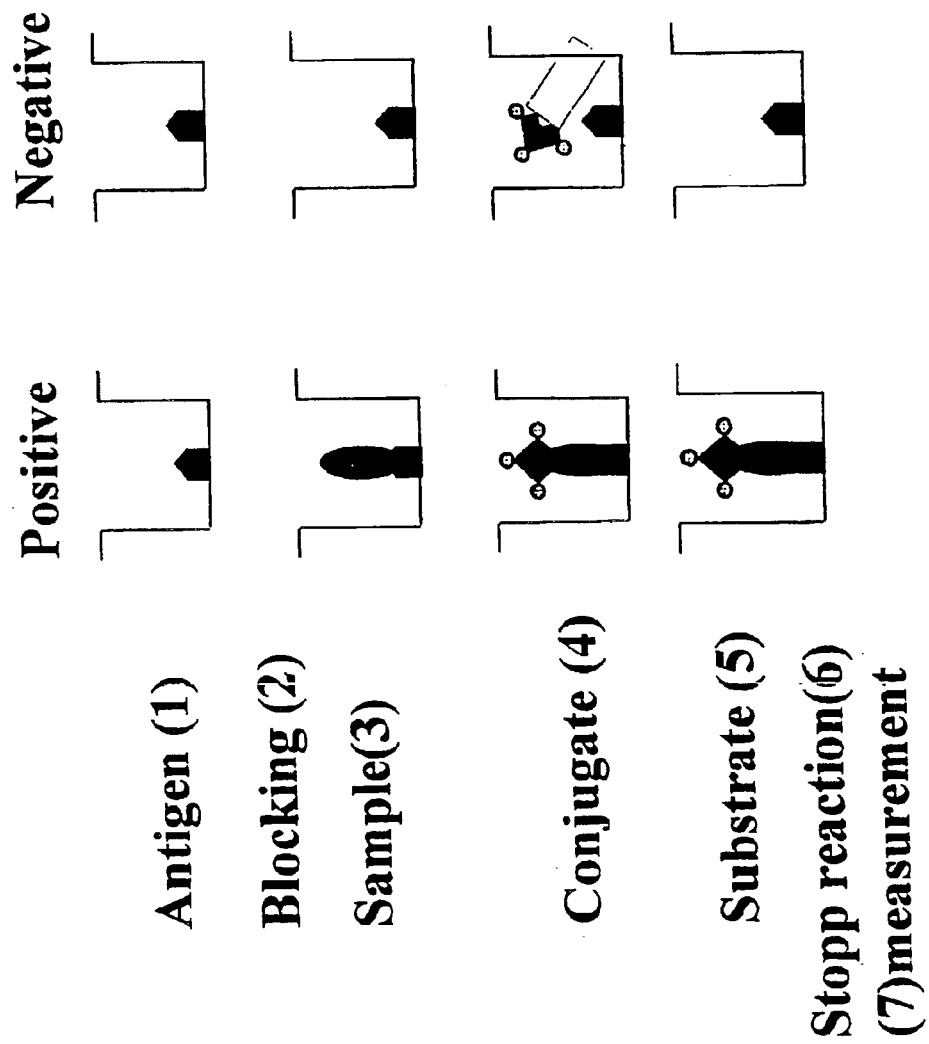

METHOD AND COMPOSITION FOR THE DIAGNOSIS OF EQUINE INFECTIOUS ANEMIA VIRUS DISEASE BY USING THE RECOMBINANT CAPSID PROTEIN VIRUS (P26)

TECHNICAL FIELD OF THE INVENTION

The present invention relates to a method of detecting antibodies against core antigen of equine infectious anemia virus (EIAV), using as antigen the recombinant protein (p26) in immunoenzymatic assays. More particularly, it relates to the use of recombinant protein p26 in kits for diagnosis of equine infectious anemia (EIA).

BACKGROUND TO THE INVENTION

The equine infectious anemia (EIA) is one of the oldest diseases caused by virus, having been described for the first time In France by LIGNEE, Rec. Med. Vet., 20:30, 1843, and recognized as viral disease by VALLEE and CARRE. Acad. Sci., 139:331–333,1904. The disease affects exclusively the members of the family Equidae presenting a worldwide distribution and of great economical importance consequently.

The EIA virus (EIAV) is classified as a lentivirus of the Retroviridae family (CHARMAN et al. J. Virol. 19(2):1073–1076,1976), it is genetic and antigenically related to the other lentiviruses that are characterized by developing persistent infection in host. The EIA has played an especially important role in comparative virology and in the studies of the acquired immunodeficiency syndrome (AIDS). Besides their morphological identity, both viruses are similar in terms of nucleotide sequences that code for structural surfaces' proteins. This group of viruses present genetic and antigenic variants during persistent infections, which are associated to the immunresponse scape. (MONTAGNIER et al. Ann. Virol., 135:119–134, 1984, MONTELARO et al. J. Biol. Chem., 259:10539–10544,1984, RUSHLOW et al. Virology, 155:309–321, 1986, STREICHER et al. J. Am. Med. Assoc. 256:2390–2391, 1986, STOLER et al. J. Am. Med. Assoc. 256:2360–2364,1986 and HAHN et al. Science, 232:1548–1553, 1986.

The transmission of EIAV occurs mainly through bites of arthropod vectors (tabanideo) which inoculate the virus into the animal's blood stream (mechanical transmission) when feeding themselves. The way of transmission is responsible for the high prevalence of EIA in areas favorable to the life cycle of vectors (ISSEL et al. Vet., 17:251–286, 1988). The EIAV can also be transmitted by the placenta and colostro of mares with high virus levels, and by needles and surgical instruments contaminated with blood (COGGINS Comparative diagnosis of viral diseases, NY, 4:646–658, 1981). The course of infection show different clinical forms of the disease (subacute, chronic and mainly inaparent or assimptomatic) in horses (ISSEL & COGGINS, J. Am. Vet. Med. Assoc. 174(7):727–33, 1979), and the most prominent signs are the feverish episodes, hemolytic anemia, anorexia, fast weight loss and ventral edema.

The laboratory diagnosis plays a decisive role in the control and the prevalence of assymptomatic carriers, non conclusive and possibility to confuse clinical diagnosis with other trypanosomiases, pyroplasmosis, leptospirosis, hepatitis and parasites.

The diagnosis of EIAV has been done though the detection of specific antibodies against surface antigens of virus present in the serum of affected animals using the Coggins or agar gel diffusion test (U.S. Pat. No. 3,929,982 and U.S. Pat. No. 3,932,601). In the Coggins test the antigen and serum sample are placed side by side in an agarose gel plate. If EIA antibodies are present in the test serum, they will form a precipitin line when diffusing toward the agarose gel This methodology is inherently insensitive since EIAV antigen preparation derived from spleen of infected animals or equine derme cultures cells may be contaminated with non-EIAV antigens during its preparation. Besides, antibodies against non-EIAV antigens may be present in the test serum and can react with the non-EIA antigens forming a variety of nonspecific precipitin lines. Even if, the prepared EIAV-antigen batches can be purified the Coggins test is laborious, time-consuming and demanding of considerable expertise in interpretation of results. The Coggins test procedure takes twenty-four to forty-eight hours for the formation of clearly visible precipitin lines delaying results.

Porter, U.S. Pat. No. 4,806,467, discloses a method for detecting the EIA virus using a competitive enzyme-linked immunoabsorbent assay incorporating a purified viral antigen and a monoclonal antibody. To obtain the antigen, the EIA virus must first be cultured. The antigen used was the p26 capsid protein of the EIAV and was obtained through (purification of the cultured virus by a variety of means) well known in the art. The technique of virus tissue cultures increases the possibility of assay yield false positive results since the virus may be contaminated with other forms of protein or oven another virus. Additionally, the EIAV is hard to culture, making the Porter's approach difficult for large scale production.

The use of a synthetic peptide in an enzyme linked Immunosorbent assay for the detection of human immunodeficiency virus (HIV) was disclosed in Shoeman, R. L. et al, Analytical Biochemistry 161:370–379 (1987).

Darrel & Peisheng, tue U.S. Pat. No. 5,427,907, discloses a method to use a synthetic peptide as the antigen in an immunoassay for the detection of antibodies against the equine inectious anemia virus in the serum of horses. This procedure includes only the search of some epitopes of a virus proteins.

It is an object of the present invention to provide an assay for the detection of the equine infectious anemia virus antibodies which may be fast, easily and quickly performed by using the stable recombinant envelope protein (rgp26) which may be produced in sufficient amounts at a low cost.

BRIEF DESCRIPTION OF THE DRAWINGS

These and other objects, features and many attendant advantages of the invention will be better understood upon a reading of the following detailed description when considered in connection with the accompanying drawings wherein:

FIG. 1 shows schematically the method of diagnosis

FIG. 2 shows the titration of positive and negative sera In Elisa with the recombinant protein p26 as antigen.

FIG. 3 demonstrates the distribution of the optical density (OD) in Elisa with the recombinant protein p26 as antigen with 84 positive and 70 negative horse serum samples, previously tested by IDGA and ELISA using EIAV-antigen produced in cell cultures

DETAILED DESCRIPTION OF THE INVENTION

It is, therefore an object of the present invention to provide a method of immunodiagnosis for EIA disease that uses the recombinant protein p26 derived from viral capsid of EIAV. The method consists of binding the recombinant antigen to solid supports (microtiter plates, tubes, beads or nitrocelullose or nylon papers or any kind that allow protein binding) and to proceed the analysis of the sera (presence of antibodies) from animals suspected of infection with the EIAV.

According to the invention, the complete amino acid sequence of recombinant p26 has been determined, and is disclosed herein as SEQ ID NO: 1.

The recombinant protein p26 is added to a solid phase support and incubated for sufficient time to ensure that protein was bound to the support. The equine test sample is added the support and incubated for a period of time sufficient to permit any EIA antibodies are removed from sample.

Labeled conjugate is added which binds to the protein-antibody complex. Following enough time to allow such binding, any unbound labeled conjugate is removed by washing labeled conjugate is added which binds to the protein-antibody complex. Following enough time to allow such binding, any unbound labeled conjugate is removed by washing. High level of bound conjugate indicates a positive result, which means presence of EIA viral antibodies. A low level of bound conjugate indicates a negative result which means absence or undetectable level of EIA viral antibodies.

A variety of commercially available solid phase supports may be used for protein binding. The direct binding of equine antibodies present in the test serum to the solid phase support is likely to result in a false positive reading. To prevent such binding, the blocking solution is used to fill any empty binding sites on the support which did not bind antibody protein. Any substance which will not react with EIA viral antibodies will function as a blocker. A conjugate is some species which will recognize and bind with the test serum EIA viral antibody.

The conjugate may be labeled using a variety of labeling means, including but not limited to: enzyme labeling, fluorescent labeling, and magnetic labeling. If enzymatic labeling is the labeling means chosen, the conjugate is labeled with an enzyme preferably select from the group consisting of horseradish peroxidase and alkaline phosphatase. Other enzymes may be used.

When an enzyme label is used, the labeled conjugate is detected by adding an amount of a substrate which will recognize and react with the enzyme label to form a product that will produce a color change visible to the naked eye. The presence of color indicates a sufficient level of test serum antibodies to indicate infection. An absence of color is an indicator of a lack of infection, as the animal did not produce a significant number of antibodies to the virus. Hence, the labeled conjugate had few antibodies, if any, to bind with and was subsequently removed from the support. There are a variety of both peroxidase and phosphatase substrates which will react with horseradish peroxidase and alkaline phosphatase enzymes, respectively to form a colored product.

A preferred peroxidase substrate is an ortho-phenylenediamine/hydrogen peroxide solution. The intensity of the color of the product may be quantified using a spectrophotometer to read absorbance. However, measuring the absorbance is not necessary to obtain an accurate reading of the results of the assay.

Figure 2:
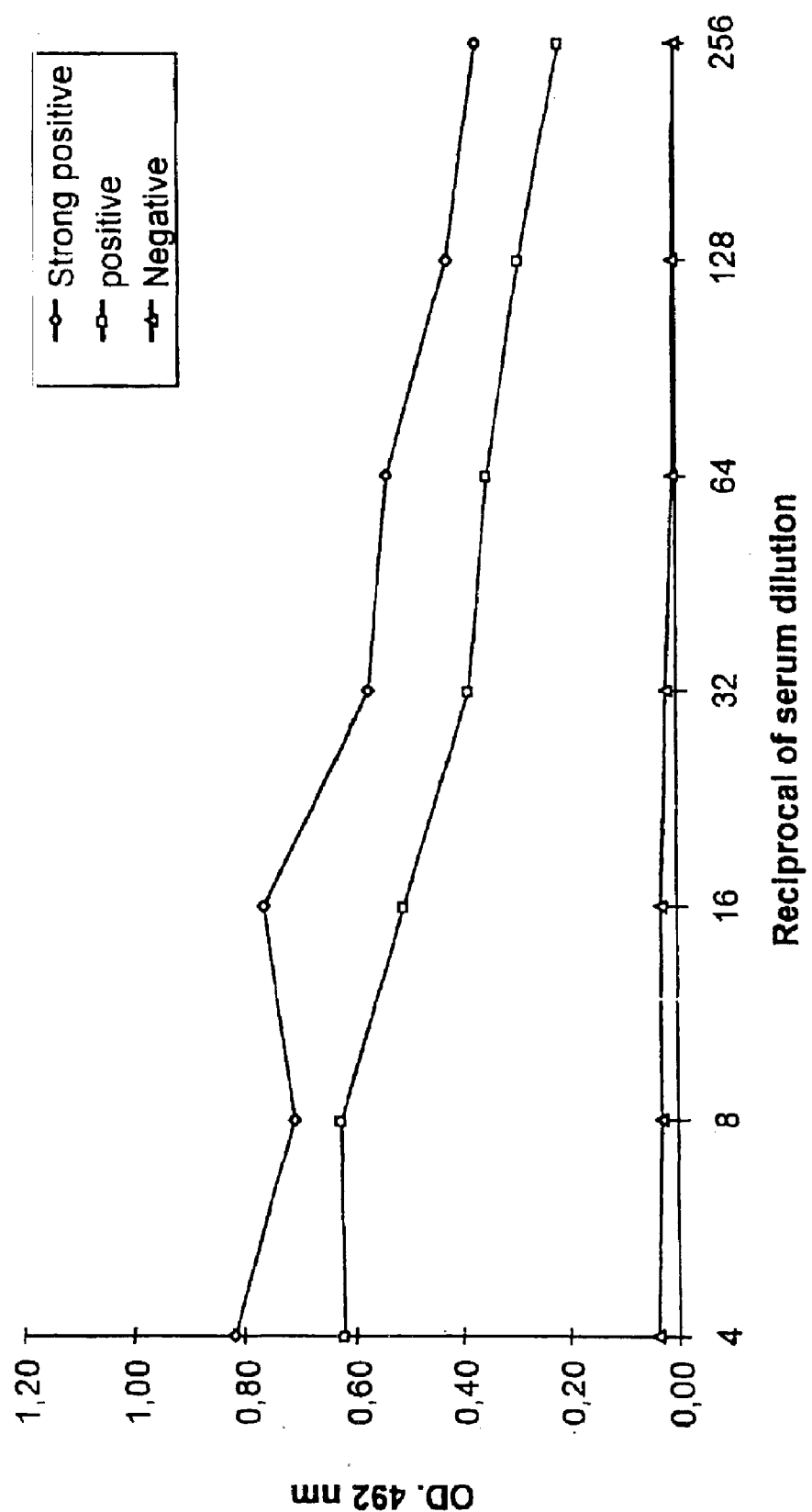

The titration of positive and negative sera in Elisa with 1 µg recombinant protein p26 as antigen. (FIG. 2) shows a detection of antibodies anti-p26 in the ELISA test using dilutions of the serum from 4 to 256 obtaining OD from 0.800 to 0.400 OD. The negative controls demonstrate that there are no non specific reaction.

Figure 3:
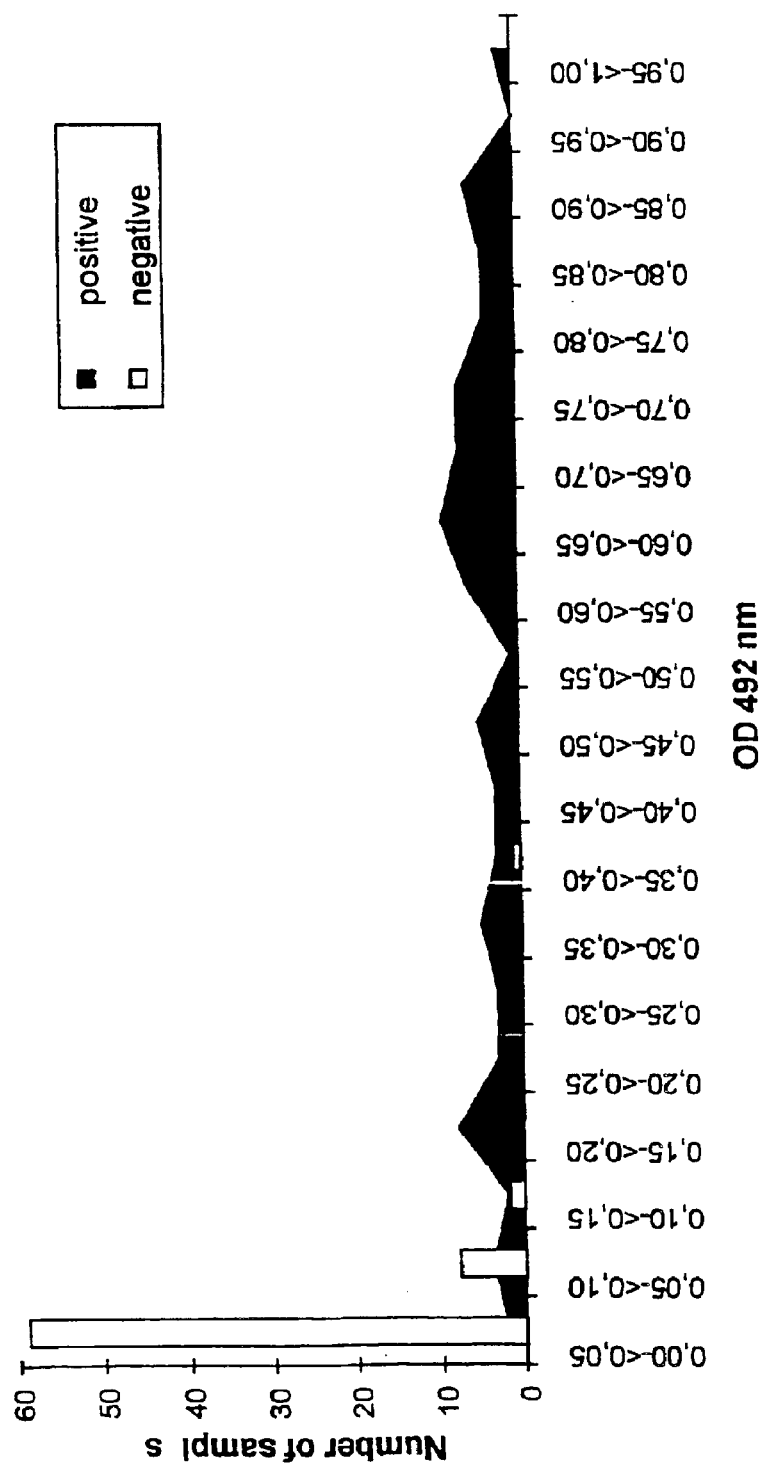

The optical density obtained when sera from 84 positive and 70 negative horses were tested is presented on FIG. 3, showing the frequency of the different optical densities obtained An animal was experimentally infected and its sera tested with the ELISA p26. FIG. 4 shows that specific antibodies were detected seven days after the infection together with the appearance of fever.

In order that this invention may be better understood the follow examples for illustrative purposes only, are described. The examples illustrate the present invention and are not intended to limit it in spirit or scope.

EXAMPLE 1

The process can be understood better through the following description in consonance with the illustration FIG. 1 where the binding of the antigen (recombinant protein p26) to the solid support (1), it is done by its dilution in carbonate buffer ($Na_2CO_3$ $O_1$ 0.1–0.5 M; $NaHCO_3$ 0. 1–0.5 M, pH 8.0–9.6), added in 24 hours microtechnique plates, tubes, beads or nitrocellulose or nylon supports, after electro- or passive transference after binding of the antigen, the support was washed of 3 to 6 times with buffer solution (0.01–0.02 M $NaH_2PO_4$, 0.01–0.02 M $Na_2HPO_4$, 0.02–0.04M KCl, 0.85–0.9% NaCl pH 7.07–7.5) and then with 0.05–0.1% of tween 20 (Buffer-Tween). To block the inespecific sites of binding (2) the used support was incubated with block solution (skimmed powdered milk 1–5% bovine, 1–5% albumin or 1–5% casein in Tween buffer) for 30–60 min at 23° C.–37° C. After a new wash of the support with Tween buffer, as described previously the positive and negative control and the serum samples were diluted in Tween buffer, to bound to the antigen linked to the solid support (3), and incubated at 23° C.–37° C. After new wash of the support with Tween buffer, the conjugate was added, where the anti-equine imunoglobuline binds to the antibodies that are tied up to the antigens (4). Conjugate can be an equine anti-imunoglobuline conjugated to the enzyme peroxidase or any other enzyme as acetylcolinesterase, lactato desidrogenase, galactosidase, glicose oxidase, alkaline fosfatase, or another. This conjugate was diluted in Tween buffer in agreement with its title and added to the support with incubation for 23° C.–37° C. for 30–60 min. A new wash of the support with Tween buffer and the development of the reaction was proceeded (5) with the enzyme of the conjugate, transforms the substrate of colorless to a red-faced product. The developing solution is composed of the substrate of the enzyme used in the conjugate that for the peroxidase for example is the ortofenilenodiamino diluted in 0.1–0.2 M phosphate or citrate buffer, pH 5.0–8.0. After the color development, that is proportional to the concentration of specific antibodies in each sample, solution of acid was used (sulfuric acid) for stopping the reaction (6), where the acid interrupts the previous reaction. For the end result the measurement (7) of the color intensity formed in each reaction (sample) was made. This reading was made visually or in spectrophotometer, in absorbance, with a specific filter for the color formed by the developing solution.

EXAMPLE 2

The kit for diagnosis of the EIAV may contain the following products: (a) the antigen recombinant p26 from EIA coated to the solid support (microplate, microtiter wells, tubes, capillary tubes, sticks, dispticks, beads) with different chemical composition (polystirene, polypropylene, polyethylene, polycarbonate, polyvinyl, polystyrene, latex, nitrocellulose, nylon; cellulose, polyacrylamyde, cross-linked dextran and microcrystalline glass (b) the anti-equine immunoglobulin conjugated with label that is selected from the group consisting of an enzyme, a fluorescent marker, avidin-biotin (c) the substrate for the label as orthophenilenodiamine and $H_2O_2$ (d) a blocking solution (0.01–0.02 M, $NaH_2PO_4$, 0.01–0.02M, $Na_2HPO_4$, 0.02–0.04 M KCl, NaCl 0.85–0.9% pH 7.0–7.5), with 0.05–0.1% of Tween 20 and skimmed powdered milk 1–5% bovine, albumin 1–5% or casein 1–5% (e) a diluent solution for specimen and conjugate ($NaH_2PO_4$ 0.01–0.02 M, $Na^2HPO_4$ 0.01–0.02 M, KCl 0.02–0.04 M, NaCl 0.85–0.9% pH 7.0–7.5), with 0.05–0.1% of Tween 20 and 1% skimmed powdered milk (f) a diluent solution for substrate 0.1 M $Na_2HPO_4$, 0.1 M $C_6H_8O_7$ pH 5.0 (f) stop solution 7N $H_2SO_4$ (g) wash solution (0.01–0.02 M $NaH_2PO_4$, 0.01–0.02 M $Na_2HPO_4$, 0.02–0.04 M KCl, 0.85–0.9% NaCl pH 7.0–7.5), with 0.05–0.1% of Tween 20 (h) positive control inactivated horse serum (i) negative control inactivated horse serum While the present invention has been described in connection with an example, it will be understood that modifications and variations apparent to those ordinary skill in the art are within the scope of the present invention.

---

We claim:

1. An immunoenzymatic assay for detecting the presence of antibodies to an equine infectious anemia virus recombinant p26 capsid antigen in equine test samples, comprising:
   (a) binding a protein having the sequence of SEQ ID NO: 1 to a solid support;
   (b) incubating a test sample of serum with the bound protein and solid support for a period of time sufficient to permit equine infectious anemia (EIA) antibodies to bind to the bound protein to form a protein-antibody complex;
   (c) removing unbound test sample;
   (d) adding a label conjugate which can bind to said protein-antibody complex;
   (e) removing unbound label conjugate; and
   (f) measuring the amount of bound label conjugate to determine the amount of bound antibody specific to the equine anemia infectious virus p26 capsid antigen in the test sample.

2. The immunoenzymatic assay according to claim 1, wherein said label conjugate is selected from the group consisting of an enzyme, a fluorescent marker, and avidin-biotin.

3. The immunoenzymatic assay according to claim 1, wherein said solid support is selected from the group consisting of polystyrene or poly propylene microtiter wells, polyethylene, polypropylene, polycarbonate, polyvinyl, polystyrene, or glass test tubes, capillary tubes, dipsticks, glass beads; latex beads; nitrocellulose, nylon; cellulose, polycrylamide, cross-linked dextran and microcrystalline glass.

4. An immunoenzymatic assay kit for detecting the presence of equine infectious anemia virus (EIAV), comprising:
   a recombinant protein p26 comprising SEQ ID No. 1 bound to a solid support and a label which is capable of binding to a recombinant protein p26-antibody complex.

5. The immunoenzymatic assay kit according to claim 4, wherein said label is selected from the group consisting of an enzyme, a fluorescent marker, and avidin-biotin.

6. The immunoenzymatic assay kit according to claim 4, wherein said solid support is selected from the group consisting of polystyrene or poly propylene microtiter wells, polyethylene, polypropylene, polycarbonate, polyvinyl, polystyrene, or glass test tubes, capillary tubes, dipsticks, glass beads; latex beads; nitrocellulose, nylon; cellulose, polycrylamide, cross-linked dextran and microcrystalline glass.

7. The immunoenzymatic assay kit according to claim 4, wherein said recombinant protein p26 is produced by *E coli* expressed by a plasmid containing the sequence of SEQ ID No. 1.

\* \* \* \* \*

SEQUENCE LISTING

<160> NUMBER OF SEQ ID NOS: 1

<210> SEQ ID NO 1
<211> LENGTH: 318
<212> TYPE: PRT
<213> ORGANISM: Equine infectious anemia virus

<400> SEQUENCE: 1

```
His His His His His His Gly Ser Pro Gly Asn Pro Leu Thr Trp Ser
 1               5                  10                  15

Lys Ala Leu Lys Lys Leu Glu Lys Val Thr Val Gln Gly Ser Gln Lys
             20                  25                  30

Leu Thr Thr Gly Asn Cys Asn Trp Ala Leu Ser Leu Val Asp Leu Phe
         35                  40                  45

His Asp Thr Asn Phe Val Lys Glu Lys Asp Trp Gln Leu Arg Asp Val
     50                  55                  60

Ile Pro Leu Leu Glu Asp Val Thr Gln Thr Val Ser Gly Gln Glu Arg
 65                  70                  75                  80

Glu Ala Phe Glu Arg Thr Trp Trp Ala Ile Ser Ala Val Lys Met Gly
                 85                  90                  95

Leu Gln Ile Asn Asn Val Val Asp Gly Lys Ala Ser Phe Gln Leu Leu
            100                 105                 110

Arg Ala Lys Tyr Glu Lys Lys Thr Ala Asn Lys Lys Gln Ser Glu Pro
        115                 120                 125

Ser Glu Glu Tyr Pro Ile Met Ile Asp Gly Ala Gly Asn Arg Asn Phe
    130                 135                 140

Arg Pro Leu Thr Pro Arg Gly Tyr Thr Thr Trp Val Asn Thr Ile Gln
145                 150                 155                 160

Thr Asn Gly Leu Leu Asn Glu Ala Ser Gln Asn Leu Phe Gly Ile Leu
                165                 170                 175

Ser Val Asp Cys Thr Ser Glu Glu Met Asn Ala Phe Leu Asp Val Val
            180                 185                 190

Pro Gly Gln Ala Gly Gln Lys Gln Ile Leu Leu Asp Ala Ile Asp Lys
        195                 200                 205

Ile Ala Asp Asp Trp Asp Asn Arg His Pro Leu Pro Asn Ala Pro Leu
    210                 215                 220

Val Ala Pro Pro Gln Gly Pro Ile Pro Met Thr Ala Arg Phe Ile Arg
225                 230                 235                 240

Gly Leu Gly Val Pro Arg Glu Arg Gln Met Glu Pro Asn Cys Val Val
                245                 250                 255

Gln Ser Phe Gly Val Ile Gly Gln Ala His Leu Glu Leu Pro Arg Pro
            260                 265                 270
```

```
-continued

Asn Lys Arg Ile Arg Asn Gln Ser Phe Asn Gln Tyr Asn Cys Ser Ile
        275                 280                 285

Asn Asn Lys Thr Glu Leu Glu Thr Trp Lys Leu Val Lys Thr Ser Gly
        290                 295                 300

Val Thr Pro Leu Pro Ile Ser Ser Glu Ala Asn Thr Gly Leu
305                 310                 315
```